US010092184B2

(12) United States Patent
Griggio et al.

(10) Patent No.: US 10,092,184 B2
(45) Date of Patent: Oct. 9, 2018

(54) LIGHTING DEVICE

(71) Applicant: NEXT SIGHT S.R.L., Pordenone (IT)

(72) Inventors: Paola Griggio, Pordenone (IT); Franco Marcori, Pordenone (IT)

(73) Assignee: NEXT SIGHT S.R.L., Pordenone (IT)

( * ) Notice: Subject to any disclaimer, the term of this patent is extended or adjusted under 35 U.S.C. 154(b) by 98 days.

(21) Appl. No.: 15/039,820

(22) PCT Filed: Nov. 27, 2014

(86) PCT No.: PCT/IB2014/002811
§ 371 (c)(1),
(2) Date: May 26, 2016

(87) PCT Pub. No.: WO2015/079315
PCT Pub. Date: Jun. 4, 2015

(65) Prior Publication Data
US 2016/0374553 A1    Dec. 29, 2016

(30) Foreign Application Priority Data

Nov. 28, 2013 (IT) .............................. VI2013A0286

(51) Int. Cl.
| A61B 3/14 | (2006.01) |
| G02B 19/00 | (2006.01) |
| G02B 3/08 | (2006.01) |
| F21V 8/00 | (2006.01) |
| A61B 3/00 | (2006.01) |
| A61B 3/12 | (2006.01) |
| G02B 27/30 | (2006.01) |
| G03B 15/06 | (2006.01) |
| F21W 131/20 | (2006.01) |

(52) U.S. Cl.
CPC .............. *A61B 3/14* (2013.01); *A61B 3/0008* (2013.01); *A61B 3/12* (2013.01); *G02B 3/08* (2013.01); *G02B 6/003* (2013.01); *G02B 19/0028* (2013.01); *G02B 19/0066* (2013.01); *G02B 27/30* (2013.01); *G03B 15/06* (2013.01); *F21W 2131/20* (2013.01)

(58) Field of Classification Search
CPC .. A61B 3/14; A61B 3/12; G03B 15/06; G02B 27/30; G02B 3/08; G02B 6/003
USPC ........................................................ 351/221
See application file for complete search history.

(56) References Cited

U.S. PATENT DOCUMENTS

| 2006/0115386 A1 | 6/2006 | Michaels |
| 2007/0019429 A1 | 1/2007 | Gasquet |
| 2009/0129230 A1 | 5/2009 | Grotsch |
| 2013/0083184 A1 | 4/2013 | Yogesan |

OTHER PUBLICATIONS

Notification of Transmittal of the International Search Report and the Written Opinion of the International Searching Authority for PCT/IB2014/002811 dated Mar. 11, 2015.
Italian Patent Office Search Report and Written Opinion dated Jan. 21, 2014 (partially in English).

*Primary Examiner* — Jack Dinh
(74) *Attorney, Agent, or Firm* — Hedman & Costigan, P.C.; James V. Costigan; Kathleen A. Costigan

(57) ABSTRACT

Lighting device (10) having a support (11), a plurality of emitting elements (12) adapted to emit light, fixed to the support (11) and each having an emission direction (A) radial to a predefined optical axis (B). The lighting device (10) is provided with a reflection surface (13) facing the emitting elements (12) and configured to reflect the light emitted in use by the latters in a direction parallel to the optical axis (B).

9 Claims, 1 Drawing Sheet

LIGHTING DEVICE

The present invention concerns a lighting device.

In particular, the present invention refers to a lighting device configured to emit a tubular light beam.

The invention lighting device is specially adapted to generate a tubular light beam having annular section, coaxial to the optical axis of an optical system of fundus camera.

A traditional fundus camera comprises an image acquisition device and an optical system of lenses adapted to collimate a light beam for the illumination of the retina and contextually adapted to focus the image of the illuminated retina onto the acquisition device.

Today an illumination device is known which comprises a flat support perpendicular to the optical axis of the lenses of the fundus camera and provided with a hole through which the same optical axis passes.

On the support, a plurality of LEDs are provided, which define as many light emission points disposed along a first ring that is coaxial with the optical axis, having a first diameter.

Such LEDs are electrically connected to a supply electronic circuit which is integrated in the support and are disposed to emit a light beam having an average direction that this perpendicular to the support.

A transparent collimation element is superimposed to the LEDs and is constituted by a light guide which has an input annular face facing the support, superimposed to the LEDs, and an emission face, annular as well, coaxial with the optical axis and having a second diameter which is smaller than the first diameter.

The input face receives the light of the LEDs according to an input direction which is parallel to the direction of the emission of light which is emitted through the emission face.

Internally, the collimation element presents two reflection surfaces, which are frusto-conical and coaxial with the optical axis.

Such two reflection surfaces are disposed in such a way to reflect the light coming from the input face towards the output face.

The problem underlying the present invention is to improve the above described traditional lighting device.

It is main task of the present invention to realise a lighting device which solves such a problem.

In the framework of such a task, it is object of the present invention to propose a lighting device which is structurally simpler than the above described lighting device.

Another object of the present invention is the realisation of a lighting device which comes out to have an optical efficiency which is larger than the described traditional lighting device.

Still another object of the present invention is to propose a lighting device proposing a technical alternative to the above described traditional lighting device.

This task, as well as these and other objects better appearing in the following, are achieved by a lighting device according to the enclosed claim 1.

Detailed features of the lighting device according to the invention are given in the dependent claims.

Further features and advantages of the invention will be better evident from the description of an embodiment, which is preferred but not exclusive, of the lighting device according to the invention, and is illustrated by way of indication but not by way of limitation in the enclosed drawings, wherein.

Figure 1:
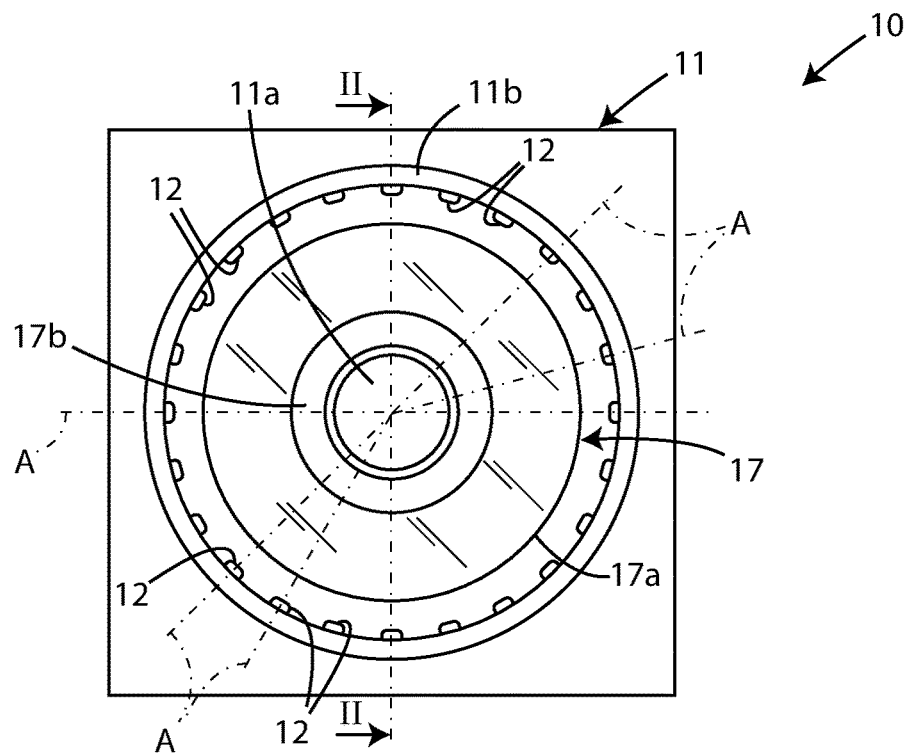
FIG. 1 illustrates in a front view the lighting device according to the invention.

With particular reference to the cited figures, it is globally indicated with 10 a lighting device comprising a support 11 and a plurality of emitting elements 12 adapted to emit light, and fixed to the support 11.

Each emitting element 12 has an emission direction A which preferably consists in the median direction of the light beam which is irradiated in use by the emitting element 12.

Advantageously, the emitting elements 12 comprise LEDs and preferably comprise first LEDs adapted to emit a visible luminous radiation and second LEDs adapted to emit an infrared radiation.

According to the invention, the lighting device then presents a peculiarity in the fact that each emission direction A is radial with respect to a predefined optical axis B, being the lighting device 10 provided with a reflection surface 13 facing the emitting elements 12 and configured to reflect the light, which is emitted in use by the latter, in a direction parallel to the optical axis B.

Advantageously, when the lighting device 10 is installed in a fundus camera, the optical axis B coincides with the optical axis of the optical system of the fundus camera.

Preferably, the support 11 has a central portion 11a permeable to the light.

Such central portion 11a can be a through hole in the support 11 or a transparent portion of the support 11 itself.

The optical axis B is advantageously incident in said central portion 11a.

Preferably, the support 11 comprises an annular collar 11b which runs circumferentially with respect to the optical axis B and protrudes from the support 11.

The emitting elements 12 are advantageously fixed on the annular collar 11b in such a way that the respective emission directions are reciprocally coplanar.

In an alternative embodiment of the invention, not shown, instead of the collar 11b, the emitting elements 12 comprise lateral emission LEDs, fixed to the support 11 in such a way that the respective emission directions are reciprocally coplanar.

Preferably, the lighting device 10 comprise collimation means placed in front of the emitting elements 12 and configured to collimate in the emission direction A the light emitted in use by each of the emitting elements 12.

The collimation means advantageously comprise lenses 15 provided with a profile chosen between:

a spherical convex profile;

an aspherical convex profile;

a profile with annular sections constituting a Fresnel lens.

The collimation means advantageously comprise lenses 15 fixed on the emitting elements 12 in such a way to collimate in the emission direction A the light emitted by each emitting element 12.

In a realisation variation of the invention, not shown, the collimation means are advantageously fixed to said support and preferably comprise lenses placed along the trajectory of the light emitted in use by the emitting elements, between the latters and the reflection surface.

Figure 2:
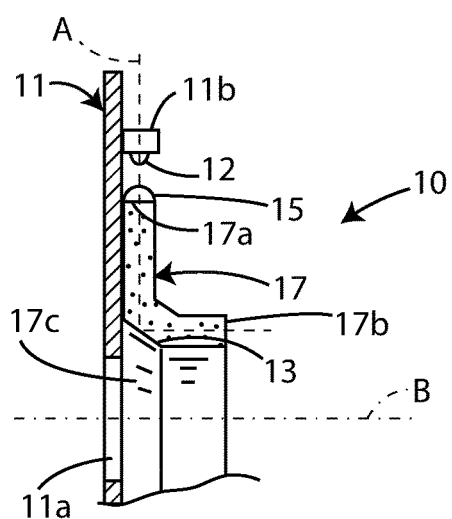
FIG. 2 illustrates a lighting device according to the invention, in the section according to the plane II-II of FIG. 1.

In an embodiment of the invention, which is given by way of non-exhaustive example in the FIGS. 1 and 2, the lighting device 10 comprises a light guide 17.

The light guide 17 and the emitting elements 12 are mutually configured and disposed in such a way that, in use, the light guide 17 preferably reflects and convey the light emitted by the emitting elements 12 in such a way to form a light tubular beam.

In order to obtain a homogeneous and tubular light beam, the lighting device 10, therefore, comprises a light guide 17 having:
- an input surface 17a, annular to the optical axis B and facing the emitting elements 12;
- an emission surface 17b annular to the optical axis B and configured to address the light parallel to the optical axis B;
- a frusto-conical internal wall 17c, annular to the optical axis B and defining the reflection surface 13.

Indeed, the particular structure of the light guide 17 allows to obtain a mixing of the luminous radiation emitted by the emitting elements 12 so that, for example, the failure of one of these would be compensated by the emission of the others, generating an attenuation of the luminous radiation exiting the light guide, which is at most slightly stronger in correspondence of the zone linearly corresponding to the emitting element which is down.

In practice, a device according to the present invention will be able to work also in the case of malfunctioning of one or more emitting elements, differently from the traditional devices.

Indeed, in a traditional device, such as that of US2013/83184, the malfunctioning of an emitting element would cause an incomplete and non-uniform illumination with a substantial lack of illumination in correspondence of the emitting element which is down.

In order to increase the illumination and energy efficiency, advantageously, the position of the lighting device 10 with respect to the light guide 17 and the structure of the latter are chosen in such a way that the input light, which in use penetrates in the light guide 17 through the input surface 17a, is reflected in a complete way by the walls of the light guide 17 itself and exit the latter only through the emission surface 17b.

In particular, the walls of the light guide 17 are preferably metallised, at least in correspondence of the internal wall 17c.

Advantageously, the emission surface 17b is configured in such a way to obtain a light beam exiting the light guide 17, having a predefined form and orientation.

Preferably, the emission surface 17b is concave or convex or prismatic.

The collimation means advantageously comprise lenses 15, integral to the light guide 17 and preferably defined by protrusions extending from the input surface 17a.

In general, according to the present invention, the emitting elements 12 and the reflection surface 13 are configured in such a way that, in use, the light emitted by the emitting elements 12 is reflected substantially once, only on the reflection surface 13.

Clearly, in case the light guide 17 is provided, the light will be marginally reflected even by internal walls parallel to the emission direction A or to the optical axis B.

It is therefore clear that the lighting device according to the invention is structurally simpler than the above described traditional lighting device.

Moreover, the lighting device according to the invention comes out to have an optical efficiency which is larger than the described traditional lighting device, having an optical path that is simpler than the traditional lighting devices.

A lighting device according to the invention constitutes moreover a valid technical alternative, structurally simpler, to the traditional lighting devices.

It is to be noted that the present lighting device, although it has been described with particular reference to the application in the field of the fundus camera, can be used, in general, in various application fields, in particular to generate a tubular luminous beam that is coaxial to a predefined optical axis.

The so conceived invention is susceptible of a number of modifications and variations, all falling within the scope of protection of the enclosed claims.

Moreover, all the details can be substituted by other technically equivalent elements.

In practice, the used materials, as well as the forms and the contingent dimensions, can be varied depending on the contingent needs and the state of the art.

Once the constructive features and the techniques mentioned in the following claims are followed by reference signs or numbers, such reference signs or numbers have been placed with the only aim of increasing the intelligibility of the same claims and, as a consequence, they do not constitute in any way a limitation to the interpretation of each element identified, by only way of example, by such reference signs or numbers.

The invention claimed is:

1. Lighting device (10) for a fundus camera, said lighting device (10) comprising a support (11) and a plurality of emitting elements (12) adapted to emit light, each having an emission direction (A) and fixed to said support (11), said emission direction (A) consisting of the median direction of a light beam which is irradiated in use by the emitting element (12) wherein each emission direction (A) of said emitting elements (12) is radial with respect to a predefined optical axis (B), said lighting device (10) being provided with a reflection surface (13) facing said emitting elements (12) and configured to reflect the light, which is emitted in use by said emitting elements (12) adapted to emit light, in a direction parallel to said optical axis (B); characterised in that said lighting device (10) comprises a light guide (17) having:
   a. an input surface (17a), annular to said optical axis (B) and facing said emitting elements (12);
   b. an emission surface (17b) annular to said optical axis (B) and configured to direct light parallel to said optical axis (B); and
   c. an internal wall (17c), frusto-conical and annular to said optical axis (B) and defining said reflection surface (13).

2. Lighting device (10) according to claim 1, characterised in that it comprises collimation means positioned in front of said emitting elements (12) and configured to collimate in said emission direction (A) the light emitted in use by each of said emitting elements (12).

3. Lighting device (10) according to claim 2, characterised in that said collimation means comprise lenses (15) provided with a profile chosen among:
   a. a spherical convex profile;
   b. an aspherical convex profile; and
   c. a profile with annular sections constituting a Fresnel lens.

4. Lighting device (10) according to claim 2, characterised in that said collimation means comprise lenses (15) positioned between said emitting means (12) and said reflection surface (13), along a trajectory run in use by the light emitted by said emitting means (12), to collimate said light.

5. Lighting device (10) according to claim 4, characterised in that said lenses (15) are fixed on said support (11) or to said emitting elements (12).

6. Lighting device (10) according to claim 1, characterised in that said lighting device (10) comprises a frusto-conical mirror defining said reflection surface (13) and coaxial to said optical axis (B).

7. Lighting device (10) according to claim 1, characterised in that said collimation means comprise lenses (15) integral to said light guide (17).

8. Lighting device (10) according to claim 7, characterised in that said input surface (17*a*) is provided with protrusions forming said lenses (15).

9. Lighting device (10) according to claim 1, characterised in that said emitting elements (12) and said reflection surface (13) are configured in such a way that, in use, the light emitted by said emitting elements (12) is reflected only once and only on said reflection surface (13).

\* \* \* \* \*